United States Patent
Dubinsky et al.

(10) Patent No.: US 9,902,996 B2
(45) Date of Patent: Feb. 27, 2018

(54) METHODS OF PREDICTING THE NEED FOR SURGERY IN CROHN'S DISEASE

(75) Inventors: Marla C. Dubinsky, Los Angeles, CA (US); Dermot P. McGovern, Los Angeles, CA (US); Jerome I. Rotter, Los Angeles, CA (US); Stephan R. Targan, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/372,359

(22) Filed: Feb. 13, 2012

(65) Prior Publication Data
US 2012/0208900 A1  Aug. 16, 2012

Related U.S. Application Data

(60) Provisional application No. 61/442,045, filed on Feb. 11, 2011.

(51) Int. Cl.
*C07H 21/04* (2006.01)
*C12Q 1/68* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
CPC ............. C12C 1/6883; C12C 2600/118; C12C 2600/156; C12C 2600/158; C12C 2537/143; C12C 2545/114; C12C 1/68; C12C 1/6886; C12C 2600/106; C12C 2600/136; C12C 2600/112; C12C 1/6806; C12C 2600/154; C12C 1/6837; C12C 2600/16; C12Q 1/6886
See application file for complete search history.

(56) References Cited

U.S. PATENT DOCUMENTS

| | | | |
|---|---|---|---|
| 6,905,827 B2 | 6/2005 | Wohlgemuth et al. | |
| 7,838,239 B2 | 11/2010 | Mitsuhashi et al. | |
| 2003/0092019 A1* | 5/2003 | Meyer et al. | 435/6 |
| 2007/0054282 A1 | 3/2007 | Liew et al. | |
| 2012/0073585 A1 | 3/2012 | Rotter et al. | |

FOREIGN PATENT DOCUMENTS

| | | |
|---|---|---|
| EP | 2005175 | 7/2011 |
| JP | 2009-535016 | 10/2009 |
| WO | 2007117611 A2 | 10/2007 |
| WO | 2010118210 A1 | 10/2010 |

OTHER PUBLICATIONS

Hirschhorn et al. (Genetics in Medicine. vol. 4, No. 2, pp. 45-61, Mar. 2002).*
Lucentini et al (The Scientist (2004) vol. 18, p. 20).*
Mummidi et al (Journal of Biological Chemistry 2000 vol. 275 No. 25 pp. 18946-18961.*
Ferguson (Gastoenterology Research and Practice vol. 2010 Article ID 539461 pub online Dec. 27, 2010).*
Alvarez-Lobos (Annals of Surgery Nov. 2005 vol. 242 No. 5 pp. 369-7000).*
Forcione (Gut 2004 vol. 53 pp. 1117-1122).*
Duerr (Science vol. 314 pp. 1461-1463 Dec. 2006).*
Alvarez-Lobos (Annal of Surgery vol. 242 No. 5 Nov. 2005).*
PCT/US2010/030359 International Search Report dated Aug. 11, 2010; 5pages.
PCT/US2010/030359 Written Opinion dated Aug. 11, 2010; 6 pages.
PCT/US2010/030359 International Preliminary Report on Patentability dated Oct. 11, 2011; 7 pages.
Barrett et al. Genome-wide association defines more than 30 distinct susceptibility loci for Crohn's disease. Nature Genetics (2008). 40(8):955-962.
Marrakchi et al. Interleukin 10 promoter region polymorphisms in inflammatory bowel disease in Tunisian population. Inflammation Research (2009). 58:155-160.
GenBank AF252829.4 Homo Sapiens chromosome 8 clone RP11-495D4 map 8q24.2, complete sequence. (2002). retrieved from the internet: <URL:http//www.ncbi.nlm.nih.gov/nuccore/24371361. 46 pages.
Picornell et al. TNFSF15 is an Ethnic-Specific IBD Gene. Inflamm Bowel Dis (2007). 13(11):1333-1338.
Vasiliauskas et al. Marker antibody expresion stratifies Crohn's disease into immunologically homogeneous subgroups with distinct clinical characteristics. Gut (2000). 47:487-496.
Wu et al. Genome-wide Gene Expression Differences in Crohn's Disease and Ulcerative Colitis from Endoscopic Pinch Biopsies: Insights into Distinctive Pathogenesis. Inflamm Bowel Dis (2007). 13(7): 807-821.
Yamazaki et al. Single nucleotide polymorphisms in TNFSF15 confer susceptibiity to Crohn's disease. Human Molecular Genetics (2005). 14(22):3499-3506.
Yeager et al. Genome-wide association study of prostate cancer identifies a second risk locus at 8q24. Nature Genetics (2007). 39(5):645-649.
Ahmad et al., Clinical Relevance of Advances in Genetics and Pharmacogenetics of IBD, Gastroenterology, 2004, vol. 126, pp. 1533-1549.
Reference SNP Cluster report for rs4855535 retrieved from: http://www.ncbi.nlm.nih.gov/SNP/snp_ref.cgi?db=human_9606&na=1&gn1=gnl%7CdbSNP%7Crs48555358cRID=2VKSYHD . . . , printed on Sep. 10, 2013, 5 pages.

(Continued)

*Primary Examiner* — Amanda Haney
(74) *Attorney, Agent, or Firm* — Wilson Sonsini Goodrich & Rosati

(57) ABSTRACT

The present invention relates to methods of predicting susceptibility to a severe form of Crohn's disease in an individual by determining the presence or absence of one or more risk variants. In one embodiment, the risk variants comprise a combination of genetic risk variants and clinical risk factors. In another embodiment, the genetic risk variants are at the IL12B genetic locus. In another embodiment, the severe form of Crohn's disease is characterized by a rapid progression to a condition requiring surgery for treatment.

16 Claims, 3 Drawing Sheets

(56) References Cited

OTHER PUBLICATIONS

GeneCards entry for BRWD1 retrieved from: http://www.genecards.org/cgi-bin/carddisp.pl?gene=BRWD1&search=brwd1, on Sep. 10, 2013, 11 pages.
Hegel, R.A., SNP Judgments and Freedom of Association, Arterioscler Thromb Vasc. Biol, 2002, vol. 22, pp. 1058-1061.
Juppner, H., Functional Properties of the PTH/PTHrP Receptor, Bone, 1995, vol. 17(2), Supplement, pp. 39S-42S.
Pennisi, E., A Closer Look at SNPs Suggests Difficulties, Science, 1998, vol. 281(5384), pp. 1787-1789.
Taylor et al., ANCA Pattern and LTA Haplotype Relationship to Clinical Responses to Anti-TNF Antibody Treatment in Crohn's Disease, Gastroenterology, 2001, vol. 120, pp. 1347-1355.

\* cited by examiner

SEQUENCE LISTING

<160> NUMBER OF SEQ ID NOS: 8

<210> SEQ ID NO 1
<211> LENGTH: 1372
<212> TYPE: DNA
<213> ORGANISM: Homo sapiens

<400> SEQUENCE: 1

```
caaaaaaaga aaataaactt gggacgttta aactttaca ttttgccata tttcaaataa    60
gatttaagat agcttaaaag aatataaaca tataagagac aatttaagtt aaaagtggaa   120
gagaggccgg gtgcggtgac tcatgcctgt aatcccagca ctttgggagg ctgaggtggg   180
tggatcactt gaggccaggg gttcgttcaa gaccagcctg gccaacatgg tgaaacccca   240
cctccactaa aaatacaaaa gtcgggcatg gtggcacatg cctgtaagtc ccagctactt   300
gggtggctgt ggcaggcaaa tcgtttgagc ccaggagatg gaggttgcag tgagtcaaga   360
tcgcaccact acattccagc ctgggtgaca gagtgagact ctgtttcaaa ataaataaa   420
ataaaataaa gtagaaaaga aacaaaaatt ataagatagg acattaaat ggagttagaa    480
atgaggctaa taataatga atatgctgca ccrtggaata ctactcagcc ataaaacaga   540
acaaaataat ggactttgca gcaacttgga tggagctgga agccattatc ttaagtgaaa   600
taattcacaa atggaaaacc aaagattgta tgttctcact tgtaaatggg agctaagcta   660
tgaggatgca aaggcataag aatgactttg gggactcaga gggaagagtg ggagggaggt   720
gaggaataaa agactacaca tattgggtac agtgcatact gcttaggtga tgggtgcatc   780
aaaatctcag aaatccggcc gggcgtggtg gctcatgcct gtaatccag cactttggga   840
ggccgaggca ggtggatcat gaggtcagga gatcgagacc atcctggcta acacggtgaa   900
accctgtctc tactaaaaat acaaaaaatt agccgggcgt ggtggcaggc acctgtggtc   960
ccagctactt cggaggctga ggcagaatgg cgtgaacccg ggaggtggaa gttgcactga  1020
gtcaagatca cgccactgca ctccagcctg ggtgacagag caagactccg tctcaaaaaa  1080
aaaaaaaaaa aaatctcag aaatccccac taaagaatgg atccatgtaa tcaaaaacta  1140
tctgtaccc caaaactatt gaaataaaa aaaatgaat gtgacacagt cctatatgta   1200
tttggcaact agcccaagt tgggttgggc tttaagcttt cttgttgtca gtgcaaatag  1260
agaaactcaa ccaactacag ttttgcaata tccacgagac aaatgtttag gaaaagtaca  1320
actacatcta acactatgtc cagaaacaat gtgtccctgg gttcttacaa ag         1372
```

<210> SEQ ID NO 2
<211> LENGTH: 701
<212> TYPE: DNA
<213> ORGANISM: Homo sapiens

<400> SEQUENCE: 2

```
atgttagtga caacccttgg aaggaattttc tctattgttc ttggtatcat ctcttgtttt    60
atttagctca gggtcactat caattgtata accaatcagg tctccatttt aattggatgc   120
caagtttacg gtacacttgt aatgtataaa ttcatttttg tgttaacctt attcttggtg   180
ttattttaat tctatgaaga mctattatgg gacaggccct gttcacatgg caacaaaagt   240
gaacaagaag acaaagtcta ttttatgttg ctactcttgt tttgcttttt ctttctcatc   300
tacttctaat ttgtgatttc ttgctataca gtaacctcct aaatcctttc aggatcaagt   360
gcataaaata agtggatatt ataaatatat atacacctaa aatagagca gcaaaataca   420
caaatcaaaa ctgacacaat tgaagggaca aatagacaat caatagcagt agttggagac   480
ttcaacaaac tgctttcaat acagtgagaa caactaagta aagatcaat aaaaagatag    540
aagtcttttt ttttttttttt tgagacagag tattgctctg tcgcccaggc tggagtgcag   600
tggcatgatc tcagctcgct gcaacctctg cctcccgggt tcaagcaatt cttctgtctc   660
agcctcccga gtagctggga ctacacatgt gtgccaccac t                       701
```

<210> SEQ ID NO 3
<211> LENGTH: 601
<212> TYPE: DNA
<213> ORGANISM: Homo sapiens

<400> SEQUENCE: 3

| | | | | | |
|---|---|---|---|---|---|
| atctttatgg | aaagatgttc | attattcact | atattgaatt | ttataatgtt | aaactctgct | 60 |
| tttctttgca | taaactatca | gagattataa | tactaaaatc | ttaaatagtt | aaattataag | 120 |
| taaattttgt | gttttcccat | atataaaagt | gatatattta | atgaatgcta | gtaatcttaa | 180 |
| actggttata | taattttata | ctacaatgag | taccttcgag | aaagcttatg | gtataagaaa | 240 |
| tactatttcc | aaaacatttt | tgttgcacat | ttttggtatt | agactcatca | ttccaatgac | 300 |
| rtctggatta | tgggaagaaa | ggagcctgac | tcttatgatg | gaataaccac | aaatcagaga | 360 |
| ggagtcacaa | tagcagctct | tggtgcagac | tgtataccga | tagttttgc | agatccagtc | 420 |
| aaaaaagcat | gtggggttgc | tcacgctggt | aagtatactt | aattaaacat | ttagaatttt | 480 |
| actcattttg | ttgtgcagga | aaaattgtaa | tttctttctg | atggacatgg | caaacagtta | 540 |
| attacattac | actgtggtaa | gtgtaatgat | gggagaggcg | gcatagtttt | attatagggg | 600 |
| c | | | | | | 601 |

<210> SEQ ID NO 4
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: n is a, c, g, or t

<400> SEQUENCE: 4

| | | | | | |
|---|---|---|---|---|---|
| caaagggctt | caaacaaatg | aaatatccat | ttagttttta | ttgaggggag | atttttatat | 60 |
| tctggtctgg | tagttttaga | aaatgtaagt | tggattttgt | ttggaacttt | attgctgagg | 120 |
| cttaatttgt | ggctcaggaa | aagaaatagt | taatatttct | tggcgaatca | aagtggattg | 180 |
| gactggttttt | tgtgcccatt | tgcttccaga | ccttgactga | cagcgtcaga | tgaagaaact | 240 |
| catcatttgg | natattagga | gatgcttgaa | acccttaga | acaggctgac | ctgggcagtg | 300 |
| tgggatgtga | ctttgggaga | tctgtttttaa | cattttttgta | aaataatatc | accatgagtg | 360 |
| ccgggctttg | cagagggaag | gtcagattcc | tgatatgaaa | ggactgagtt | attaaaaaca | 420 |
| aactgaaggc | tagaagcgaa | gttaacactt | gagaaattaa | aggccatgat | ggtgaacttg | 480 |
| actccgggct | ttcagctttt | g | | | | 501 |

<210> SEQ ID NO 5
<211> LENGTH: 801
<212> TYPE: DNA
<213> ORGANISM: Homo sapiens

<400> SEQUENCE: 5

| | | | | | |
|---|---|---|---|---|---|
| aattcttata | gataaatgtc | ctctaatttg | tttctgaaat | gccaaatcta | acttaagcaa | 60 |
| tttatgacca | ctattttatc | agtgcttaaa | tttaattttc | cttcttcata | gttagtaccc | 120 |
| actgtacaca | tttctatatt | aatatacata | catatttaaa | ttaatgtaac | attaaatcta | 180 |
| taagcataac | caagttaatt | ataactatgt | gataaaatat | gcaaattatt | ttttagacag | 240 |
| tgactctttc | aaatatccaa | ctgaattata | taaataaaac | atgaatgaca | aatttttag | 300 |
| ttgtttgtca | catattacaa | ccattctata | tgttattcat | tttccaaata | taaagagtt | 360 |

| | |
|---|---|
| accattacta gatggaaaat tatattcaga aatgcagaca ygtccttggt aggaaaaaga | 420 |
| tagaaacgca caacgagctt cactcactaa accaaatttc ttaaatttca aaaagaccca | 480 |
| ttattcacag gtcaaatttg tcccttgatc agtatacaga aaacaataag gtttagtcat | 540 |
| aaacagtaaa gcagcatgtc tggaaggaaa gagactagaa atgaaacaaa atgagatatg | 600 |
| ggccgtctaa ggctacccca gtcctcactt tcaccccct tcacctagac gagtacatgc | 660 |
| tgaacaagca ccaaaaacaa ccaataaatg aaaggaaact caaaggtcac ttggggtcat | 720 |
| tattttcaca tacctttgaa taatgagagc atcacatgtc agccagagga gaacaaaatg | 780 |
| tcacattctc cagctaaagg t | 801 |

<210> SEQ ID NO 6
<211> LENGTH: 1001
<212> TYPE: DNA
<213> ORGANISM: Homo sapiens

<400> SEQUENCE: 6

| | |
|---|---|
| gtgctgagaa ctcacaaata ctcatttcca gcctggacct ctccccagat tcacagttcc | 60 |
| acctgcctac agtcttctcc acttaagtgc ttaaaaggca tctcacactt acatccaaaa | 120 |
| ccgtattcct tatctcccca caaaacatgc tccatctgta cgcttccatt cagaaaatgg | 180 |
| caattccatc ctcccagttg ctcaggccaa aactgggaat cttcctgctg ctcccagcca | 240 |
| actctgtctc ctagttcaca gcttcagctc ctttcttttt aacctgcccc agtcaggttc | 300 |
| taaacccatt cttttaatc tctcacttcc aatccatcag caaatcctcc atgctactgc | 360 |
| tctggtccaa gccaccattg tctcttgcca agatttctgc catagcctcc taactggttc | 420 |
| tactcttct ctcagtttat tctcaacaca gcatccagag tgatcctgtt aaaatgtgag | 480 |
| ttacatcatg tcacttctct ktaaaaaacc ctctagtggc ccctgtctca gaatcagagc | 540 |
| ccaagttcac acaaggacct cccttgaatg ccgtgaacac tgtggagcct ctcactacct | 600 |
| ctctgatccc tctcctgctt ctcccttatt ctctctactc tggctacacc ccctcctca | 660 |
| cttatctgtt aacatgtcag acaggccctc actgccaggc tgttgcactt gccattccct | 720 |
| ccacctggga agcttcttcc ccgttaattc tcagggctca tgtcctcact tttttcaggt | 780 |
| aactttgttc ataatttacc ttctcaggtg tctagccttc tctggacaca cattttagaa | 840 |
| tttttacacg ccttctcacc ttctgcccca atattcctta cctctctctc ctgccttatt | 900 |
| ttttcctccc taggatttac cacttctgat tcctatattt ttaatttatg tatccttgtta | 960 |
| gtttttggac tcttcactac caccaccgcc ccaccccct a | 1001 |

<210> SEQ ID NO 7
<211> LENGTH: 501
<212> TYPE: DNA
<213> ORGANISM: Homo sapiens

<400> SEQUENCE: 7

| | |
|---|---|
| tcactatgta ccagaattct tgtggaggt cagtagtcaa gttagtcaaa ttttctcaac | 60 |
| ttaaatataa aagctatatt tttcacagag gctattattg ataaaattat ggtccccaac | 120 |
| attagtgcct ggcaaatggc ttgcactata gaagtatttg ttgaataaat gaattgaggg | 180 |
| taattaataa taagttcatt gttttatttta ttaagattag ttcaaaacag ttctccttaa | 240 |
| aattatgctg matttgtaat agtttgaaac taattctaat cttatttgaa gtatgcctca | 300 |
| tttactctat ttattggtct gatatgttat gaatgtattg gaaaatgtca ctttcgaagg | 360 |
| aataaacatc tctggaaaaa cggtaacaat attgactctt caggtctctt ggattggatt | 420 |

| | |
|---|---|
| tcagctagga ggtgggagtt cagactgtct cccatgccag agaactataa ccagtaattg | 480 |
| ttaaccttga tctgtgactt c | 501 |

<210> SEQ ID NO 8
<211> LENGTH: 3959
<212> TYPE: DNA
<213> ORGANISM: Homo sapiens

<400> SEQUENCE: 8

| | |
|---|---|
| catcaaatcg ggagtgcaca ctcccctctc atcctagctg gtacacact ccctctcat | 60 |
| cctagctggg tccttcaccc ctgccatatt tgaatgagtt tatatgtcca cctcggttcg | 120 |
| ttgcttacct ggattgtctc aaaaaatgtc tatcttgtcc aggcacagcg gctcacgcct | 180 |
| gtaatcccag cactttggga ggccgaagtg ggtgggtcac ctgaggtcag gagttcgaga | 240 |
| ccagcctggc caacatgata aaccctgtc tctactaaaa atacaaaaaa ctagccgtgt | 300 |
| gcaggggcag acacctgtaa tctcagctac ttgggaggct gaggtgggag gatcgcttga | 360 |
| acccaggagg tggaggttac agtgagccaa gatcacacca ctgtactcca gccgggacga | 420 |
| cagagtgaca gagattccat ctcaaaaaaa aaaagaaaa tgtctgtttt acagttggtt | 480 |
| agttcaaatc aagtttggtt gatgcgtctc ataaatcttt ttatctgcaa gtttccccct | 540 |
| tccttttttc atggcatgta tttgttaaag aaactgggta agccaggcat ggtggctcac | 600 |
| acttgtcatc ccagcgcttt gggaagccaa ggcggggaga tcacttgagg tcagaagttt | 660 |
| gagaccagcc tggcaacat agcgaaaccc catctctacc aaagatataa aaaattagcc | 720 |
| aggcatggcg gcatatgcct gtagtcacag ctacttggga ggctgaagtg ggaggatcac | 780 |
| ttgagtctgg gaagcagagt ttgcagtgag acaagatcat gccactgagc aacagagtga | 840 |
| gaccctgtct caaaaaaaaa aaaatgaag cagggtcatt tgttctgtag aaatttccat | 900 |
| attctgtatt tgggtgattg catccttgtg gtattgaata tatttctcta atctctgtat | 960 |
| ttcttatgaa ctattatatc taggtgagat gctggccagt acaactttct gctctgatgg | 1020 |
| aaccatgcta gatctgcgct tcccactttg tagccagtgg tcatgcattg ctatggagca | 1080 |
| ttcaaaatgt ggctaaggta actcaattgt ctatttcatt tcatttcttt tttttttttt | 1140 |
| ttttttccg agacagagtc tcactctgtt gcccaggctg gagtgcagtg cccaatctc | 1200 |
| ggctcgctgc aacctctgcc tcctgagttc aagtggttct cttgcctcag cctcctgtgt | 1260 |
| agctgggatt acaggcattc accaccacac atggctagta ttttttttt ttttagtaga | 1320 |
| gatgaagttt caccatgttg gccaggctgg tctcaaactc ctgacctcag gtgatccatc | 1380 |
| cacctcaacc tcccaaagtg cttgattaca ggcatgagcc accacgccca gcctcatttc | 1440 |
| attttaagat ttttaacttt ttttttttc aagacggagt cttgccctgt cacccaggct | 1500 |
| ggagtgcagt ggtgcgatct ggctcacca caacctctac ctgctgggtt caagcgagtc | 1560 |
| tcctgcttca gcctcccaag tagctgggat tacaggtgca tgccaccacg cccagctaat | 1620 |
| tttgtatttt tagtagagac agggtttcgc catgttggcc aggctggtct cgaactcctg | 1680 |
| acctccggtg atctgcccgc tttggcctcc caaagtgctg ggattacagt gtgagccacc | 1740 |
| gtgcctggcc tttaactttt attttagatt cgggggtaca tgcgcagatt tgttacatag | 1800 |
| gtaaactcat gtcatggggg tttgctgtat agattatttc atcacccagg aattacgccc | 1860 |
| agtattcaat agttaccttt tctgctcctc tcctcccacc ctccaccgtc agatagaccc | 1920 |
| cagcatctgt tgtttccttc tctgtgttta taaattctta tcatttagct cccacttata | 1980 |

```
agtgagaacc tgtgttttct gttcctgtgt tagtttccta aggatgatgg cctccatctc    2040
catccatgtt cccacaaaag acatgatctt tttcatggct gcataatttt attttaattc    2100
attttaattt tgagtggcta ttatattgga cagcacatat tcagaggctt gattgrattc    2160
agattccgct ttctttggca agactacttc acagatgatg ttgtgtgtcc atgtacattt    2220
tagaataagt tttagatctt ctgccaggca tggtaactca cgcctgtaat cccagcactt    2280
tgggaggctg aggcgggtgg atcacttgag gccaggcatt cgagagcagc ctggccaaca    2340
tggtgaaacc ccgtctgtaa taaaaataca aaaattagcc aggcgtgctg gtgcatgcct    2400
gtagccccag ctacttggga ggctgaggca ggagaatctc ttgaacccag gaggtggagg    2460
ttgcagtgag ccaagatcgt gccactgcac tccagcctgg gcgatagagc aagaccctgt    2520
ctcagaaata ataataataa caataagttt taggccttaa aaattccacc tggattgggg    2580
gacagggaat tgaaaggtat aggatttctt tcaagatgat gagaatattc tggaattaga    2640
tagcggtgat ggttgtgcaa tattatgaat attctaagaa ctactgactt acacacttta    2700
aaatggtaaa aattctgaat gttatgttag gtgaattta tctcaaaaaa attttttaa     2760 ttctaattgg aattttgatt gagattgaat tcaataatta gtttattaat tttgtgaaat    2820
ttggcttctt tgtaatatta agttggtcat taaagataat gaacttgagc ccaggagttt    2880
gtgaccagcc tgggcatcaa tagccagatc ccatccccaa aaaacatttt taaaaattag    2940
ccaggcctgg gctgggcgcg gtggctcaca cctgtaatcc cggcactttg ggaggccgag    3000
gcgggtggat cacaaggtca ggagatcgag acctggctaa catggtgaaa ccccgtctct    3060
actaaaaata caaaaaatta gccaggcgtg gtggcgggca cctgtagtcc cagctactca    3120
ggaggctgag gcaggagaat ggcgtgaacc gggaggcaga gcttgcagtg agccaagatc    3180
gcaccactgc actccagcct gggcaacaca gcaagtctcc gcctcaaaaa aaaaaaaatt    3240
agccaggcct gtctgggcgt ggtggttcat gcctgtaatc ccagcacttg gggaggccga    3300
ggcgggcgga tcacctgagg tctggagttc aagaccagcc tgaccaacat ggagaaaccc    3360
catctctact aaaaatacaa aagccaggtg tggtggcgca tgcctgtaat cccagctact    3420
cgggaggctg aggcaggaga gtcgcttgaa cccaggaggc ggtgtttgcg ataagctgag    3480
atcgtgccat tgcacttcag cctgggcaac aacagtgaaa ctccatctca aaaaaaaaac    3540
aaaaaaaact agctggtgcc tgtaatccca gctgcttaga aggctgacgt agaaggattg    3600
cttgaaccca ggagttacag cgtgcaatga gccatgatca caacactgca ctccagcctg    3660
ggtgacagag tgagacctta tctcaaaaaa aaaaaaaaaa aaaaaaaacc actggaaaca    3720
gccaagagat ccttcactca ttcatacagt ggaacgttaa tcagcaattc taaaaatgag    3780
ctatcaagtc acaaaaagac aaagaagaac cttaacacaa aataacacag aggaacctta    3840
aatgcatatt gctaagtgat agaagtcagt ctcaaaagac tatatactgt attattccat    3900
ccacatgaca ttctggaaaa gataaaacca tagggacagt aaaaagatta gtgattagc     3959
```

METHODS OF PREDICTING THE NEED FOR SURGERY IN CROHN'S DISEASE

CROSS-REFERENCE TO RELATED APPLICATIONS

This application makes a claim of priority to U.S. provisional patent application No. 61/442,045, filed on Feb. 11, 2011, the contents of which are hereby incorporated by reference in their entirety.

STATEMENT REGARDING FEDERALLY-SPONSORED RESEARCH

This invention was made with Government support under Grant No. DK066248 awarded by the National Institutes of Health. The Government has certain rights in the invention.

BACKGROUND

The following description includes information that may be useful in understanding the present invention. It is not an admission that any of the information provided herein is prior art or relevant to the presently claimed invention, or that any publication specifically or implicitly referenced is prior art.

Crohn's disease (CD) is a disease of diverse clinical phenotypes and patients with complicated disease phenotypes such as those with stricturing and/or internal penetrating disease behaviors often require surgical intervention. Over a 10 year period, approximately 80% of patients can expect to develop a complication and close to 50% of CD patients will progress to surgery (1, 2). This is in contrast to the small percentage of patients presenting with a complication, and requiring surgery at time of diagnosis. One of the biggest challenges facing clinicians today is predicting which patients will progress to complication resulting in intestinal resection. The identification of these "rapidly progressive" patients early in the course of their disease may assist in the decision regarding the early introduction of effective intervention strategies and customizing therapies based on risk of underlying disease. Those at highest risk of disease complication may well benefit most from early use of immunomodulators and/or biologic therapies. Despite major advances in genome discovery, there have only been a few studies that have considered the role of genetics in determining disease behavior. Variation in NOD2/CARD15 has been shown to be associated with stricturing CD, need for surgery as well as surgical recurrence (13-18). Serological immune markers have been shown to predict more aggressive disease. Recent genome-wide association (GWA) studies have identified multiple IBD susceptibility loci although their phenotypic consequences remain unknown. The ability to identify patients with Crohn's disease (CD) who are at highest risk for rapid progression to surgery would be invaluable in guiding initial therapeutic choices.

SUMMARY OF THE INVENTION

Various embodiments include a method of diagnosing susceptibility to a severe form of Crohn's disease in an individual, comprising obtaining a sample from the individual, assaying the sample to determine the presence or absence of one or more risk variants at the IL12B genetic locus, and diagnosing susceptibility to a severe form of Crohn's disease in the individual based on the presence of one or more risk variants at the IL12B genetic locus. In another embodiment, the severe form of Crohn's disease is characterized by a rapid progression to a condition requiring surgery for treatment. In another embodiment, the method further comprises determining the presence of one or more clinical, serologic and genetic risk factors. In another embodiment, the method further comprises determining the presence of anti-ASCA, pANCA, anti-Cbirl, anti-OmpC and/or anti-I2. In another embodiment, the method further comprises determining the presence of one or more risk variants at the NDFIP1, C13orf31, SMAD3, 21q21, IBD5, CACNA2D1, ZNRF1, and LDHD genetic loci. In another embodiment, the one or more risk variants comprise SEQ ID NO: 1. In another embodiment, the one or more risk variants comprise SEQ ID NO: 2, SEQ ID NO: 3, SEQ ID NO: 4, SEQ ID NO: 5, SEQ ID NO: 6, SEQ ID NO: 7, and SEQ ID NO: 8.

Other embodiments include a method of prognosing Crohn's disease in an individual, comprising determining the presence of a risk variant at the IL12B genetic locus and one or more risk factors in the individual comprising a diagnosis of Crohn's disease in the small bowel location, age of diagnosis, and/or risk serological factors, and prognosing a severe form of Crohn's disease characterized by a rapid progression to conditions associated with requiring surgery for treatment in the individual based on the presence of a risk variant at the IL12B genetic locus and one or more risk factors in the individual. In another embodiment, the method further comprises determining the presence of one or more risk variants at the genetic loci of NDFIP1, C13orf31, SMAD3, 21q21, IBD5, CACNA2D1, ZNRF1, and/or LDHD. In another embodiment, the risk serological factors comprise anti-ASCA, pANCA, anti-Cbirl, anti-OmpC and/or anti-I2. In another embodiment, the one or more risk variants comprise SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

Other embodiments include a method of treating Crohn's disease in an individual, comprising diagnosing susceptibility to a severe form of Crohn's disease in the individual based on the presence of one or more risk variants at the IL12B genetic locus, and treating the individual. In another embodiment, the severe form of Crohn's disease is characterized by a rapid progression to a condition requiring surgery for treatment. In another embodiment, diagnosing susceptibility to a severe form of Crohn's disease further comprises determining the presence of one or more clinical, serologic and genetic risk factors. In another embodiment, diagnosing susceptibility to a severe form of Crohn's disease further comprises determining the presence of anti-ASCA, pANCA, anti-Cbirl, anti-OmpC and/or anti-I2. In another embodiment, diagnosing susceptibility to a severe form of Crohn's disease further comprises determining the presence of one or more risk variants at the NDFIP1, C13orf31, SMAD3, 21q21, IBD5, CACNA2D1, ZNRF1, and LDHD genetic loci. In another embodiment, the one or more risk variants comprise SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in the referenced figures. It is intended that the embodiments and figures disclosed herein are to be considered illustrative rather than restrictive.

DESCRIPTION OF THE INVENTION

Figure 1A:
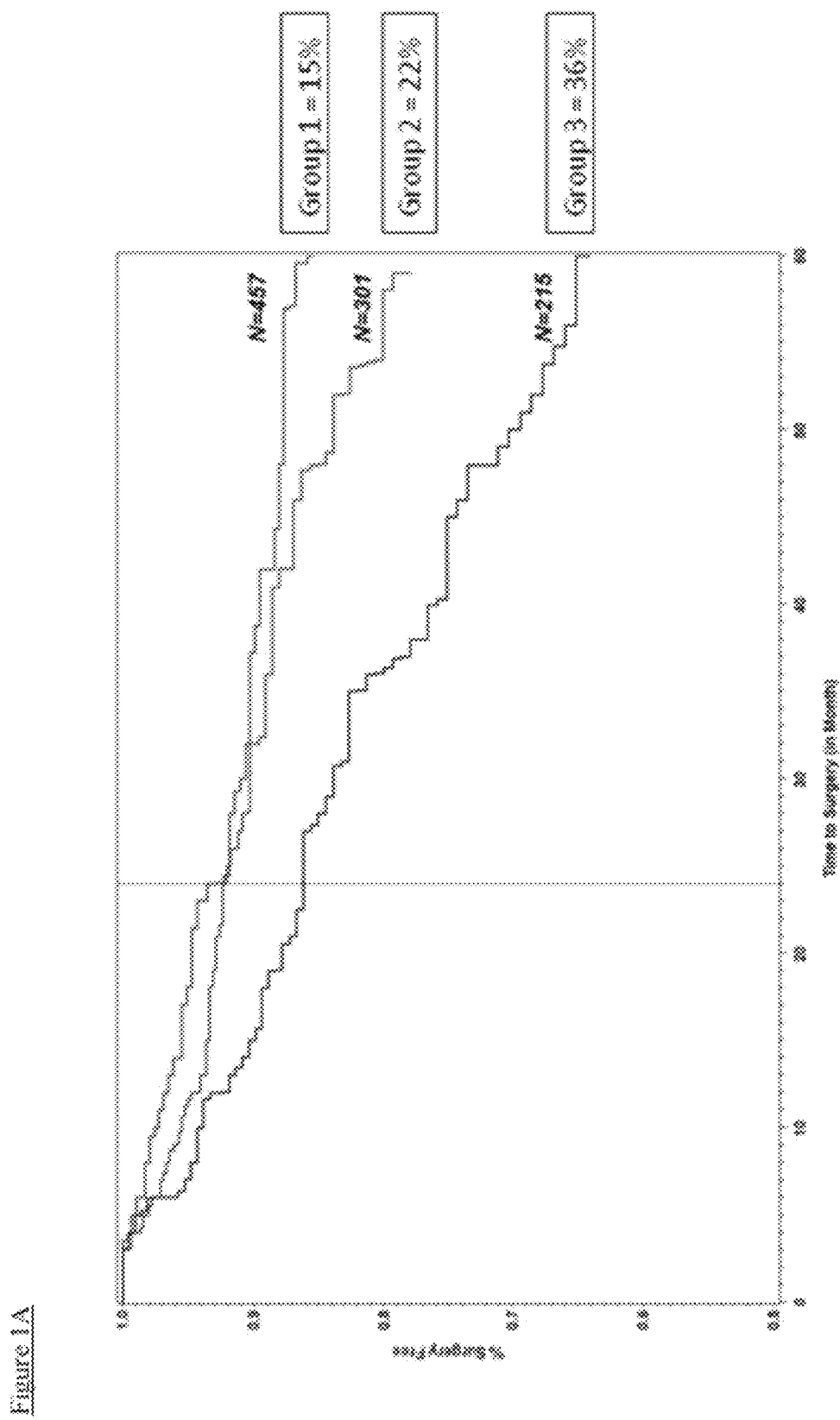
FIG. 1A illustrates, in accordance with an embodiment of the invention, survival curves for three risk strata in the inventive model.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Haplotype" as used herein refers to a set of single nucleotide polymorphisms (SNPs) on a gene or chromatid that are statistically associated.

"GWAS" as used herein means Genome-Wide Association Study.

"Risk" as used herein refers to an increase in susceptibility to IBD, including but not limited to CD and UC.

"Protective" and "protection" as used herein refer to a decrease in susceptibility to IBD, including but not limited to CD and UC.

"CD" and "UC" as used herein refer to Crohn's Disease and Ulcerative colitis, respectively.

As apparent to one of skill in the art, there are many examples of the various single nucleotide polymorphisms (SNPs) and genetic variants referenced herein. Examples of genetic variants rs6556412, rs11167764, rs3764147, rs16950687, rs1736148, rs12521868, rs11978472, and rs7195303 are provided herein as SEQ ID NO: 1, SEQ ID NO: 2, SEQ ID NO: 3, SEQ ID NO: 4, SEQ ID NO: 5, SEQ ID NO: 6, SEQ ID NO: 7 AND SEQ ID NO: 8, respectively, although the genetic variants are in no way limited to those specific sequences disclosed.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

The inventors performed a genome-wide association study testing autosomal single nucleotide polymorphisms (SNPs) on the Illumina HumanHap300 Genotyping Bead-Chip. Based on these studies, the inventors found single nucleotide polymorphisms (SNPs) and haplotypes that are associated with increased or decreased risk for inflammatory bowel disease, including but not limited to CD. These SNPs and haplotypes are suitable for genetic testing to identify at risk individuals and those with increased risk for complications associated with serum expression of Anti-Saccharomyces cerevisiae antibody, and antibodies to 12, OmpC, and Cbir. The detection of protective and risk SNPs and/or haplotypes may be used to identify at risk individuals predict disease course and suggest the right therapy for individual patients. Additionally, the inventors have found both protective and risk allelic variants for Crohn's Disease and Ulcerative Colitis.

Based on these findings, embodiments of the present invention provide for methods of diagnosing and/or predicting susceptibility for or protection against inflammatory bowel disease including but not limited to Crohn's Disease and ulcerative colitis. Other embodiments provide for methods of prognosing inflammatory bowel disease including but not limited to Crohn's Disease and ulcerative colitis. Other embodiments provide for methods of treating inflammatory bowel disease including but not limited to Crohn's Disease and ulcerative colitis.

The methods may include the steps of obtaining a biological sample containing nucleic acid from the individual and determining the presence or absence of a SNP and/or a haplotype in the biological sample. The methods may further include correlating the presence or absence of the SNP and/or the haplotype to a genetic risk, a susceptibility for inflammatory bowel disease including but not limited to Crohn's Disease and ulcerative colitis, as described herein. The methods may also further include recording whether a genetic risk, susceptibility for inflammatory bowel disease including but not limited to Crohn's Disease and ulcerative colitis exists in the individual. The methods may also further include a prognosis of inflammatory bowel disease based upon the presence or absence of the SNP and/or haplotype. The methods may also further include a treatment of inflammatory bowel disease based upon the presence or absence of the SNP and/or haplotype.

In one embodiment, a method of the invention is practiced with whole blood, which can be obtained readily by non-invasive means and used to prepare genomic DNA, for example, for enzymatic amplification or automated sequencing. In another embodiment, a method of the invention is practiced with tissue obtained from an individual such as tissue obtained during surgery or biopsy procedures.

As disclosed herein, the inventors identified genetic and phenotypic associations with need for surgery and time to surgery within 5 years of diagnosis, and built a predictive model for need for surgery. The ability to identify patients with Crohn's disease (CD) who are at highest risk for rapid progression to surgery is invaluable in guiding initial therapeutic choices.

As further disclosed herein, the need for surgery was defined as intestinal resection within 5 years of diagnosis. Genotyping was performed on 1103 subjects using Illumina-based Genome-wide technology. Univariate and multivariate analyses tested genetic associations with need for surgery. Time to surgery was analyzed using Cox-proportional hazard. All analyses were performed by testing known IBD susceptibility loci (n=74) and also by performing a GWA study. Clinical and serologic immune phenotypes as measured by antibody sum were included in the logistic regression analyses and used to build a predictive model of need for surgery.

As further disclosed herein, the inventors found that surgery occurred within 5 years of diagnosis in 39% of total subjects. The median time to surgery was 6 months. In the univariate analyses, four known CD susceptibility loci (Table 2 herein) were associated with need for surgery within 5 years ($p<0.05$). The HLA region was the only known susceptibility loci associated with time to surgery (p=0.02). GWA revealed 16 putative loci associated with need for surgery and 51 with time to surgery at a level of nominal association at the genome-wide level ($p<5\times10^{-5}$). GWA identified SNPs at chromosome (chr.) 4q31 and at chr. 7p21 (containing the glucocorticoid induced transcript 1 gene) showed the most significant association with need for surgery within 5 years (Odds ratio [OR]=1.8; $p=1.4\times10^{-7}$) and time to surgery (Hazard Ratio [HR]=1.7; $p=1.0\times10^{-7}$), respectively. Two loci: rs6556412 (IL-12B, chr. 5q33) (OR=0.74; p<0.001) and the chr. 4q31 region (OR=1.51; p=0.003) remained independently associated with surgery in the logistic regression analyses. Small bowel location (OR=3.2; p<0.0001), age at diagnosis (OR=2.88; p<0.0001) and antibody sum (OR=1.64; p<0.0001) were also associated with need for surgery. A predictive model for surgery incorporating all 5 variables had an area under the curve of 0.770. Thus, the inventors found IL12B is associated with need for surgery in CD. The identification of genetic, clinical and immune risk factors that can predict need for surgery can help clinicians and patients choose appropriate treatments based on an individual's risk of early surgery.

Furthermore, the inventors performed additional studies with the objective to identify associations between known and novel CD loci with resective CD surgery, and develop predictive models for surgery using a combination of phenotypic, serologic and genetic variables. As further disclosed herein, the inventors found surgery occurred within 5 years in 21% of subjects at a median time of 12 months. Four susceptibility loci were associated with surgery (IL12B, C13orf31, 21q21, IBD5). GWA identified novel putative loci associated with surgery, 7q21 (CACNA2D1) and 16q23 (ZNRF1, LDHD). The most predictive model for surgery which included clinical, serologic and genetic factors had an AUC of 0.78. Forty percent of patients in the highest risk group progressed to surgery within 60 months in the best predictive model. In conclusion, the inventors found that progression to surgery is faster in CD patients with both genetic and clinical risk factors, and that IL12B is independently associated with need and time to surgery in CD patients.

In one embodiment, the present invention provides a method of predicting a susceptibility to a severe form of Crohn's disease in an individual by determining the presence or absence of one or more risk variants at the NDFIP1, C13orf31, IL12B, SMAD3, 21q21, IBD5, CACNA2D1, ZNRF1, and LDHD genetic loci, where the presence of one or more risk variants at the NDFIP1, C13orf31, IL12B, SMAD3, 21q21, IBD5, CACNA2D1, ZNRF1, and LDHD genetic loci is indicative of susceptibility to the severe form of Crohn's disease. In another embodiment, the one or more risk variants are listed in Tables 1, 2(a) and/or 2(b) herein. In another embodiment, the one or more risk variants are listed in Tables 4 and/or 5 herein. In another embodiment, the risk variants comprise genetic risk loci, clinical risk factors, serological risk markers, and combinations thereof. In another embodiment, the severe form of Crohn's disease is characterized by a rapid progression to a condition requiring surgery for treatment. In another embodiment, the individual has been diagnosed with Crohn's disease. In another embodiment, the condition requiring surgery for treatment occurs within a year of an initial diagnosis of Crohn's disease. In another embodiment, the condition requiring surgery for treatment occurs within 6 months of an initial diagnosis of Crohn's disease.

In another embodiment, the present invention provides a method of diagnosing a severe form of Crohn's disease in an individual by determining the presence or absence of one or more risk variants, and diagnosing the severe form of Crohn's disease in the individual based on the presence of one or more risk variants. In another embodiment, the risk variants comprise genetic risk loci, clinical risk factors, serological risk markers, and combinations thereof. In another embodiment, the severe form of Crohn's disease is characterized by a rapid progression to a condition requiring surgery for treatment.

In another embodiment, the present invention provides a method of treating a severe form of Crohn's disease in an individual by diagnosing a severe form of Crohn's disease and treating the individual.

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature, "Nucleic Acids Research 28:655-661 (2000)). Minor grove binders include, but are not limited to, compounds such as dihydrocyclopyrroloindole tripeptide (DPI,).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against CD in an individual may be practiced using one or any combination of the well-known assays described above or another art-recognized genetic assay.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

TABLE 1

Table 1: Univariate GWAS association (0-60 gwas sign SNPs n = 16)

| CHR | SNP | BP | A1 | TEST | NMISS | OR | STAT | P |
|-----|-----|-----|-----|------|-------|-----|------|-----|
| 4 | rs361147 | 153110013 | C | ADD | 1022 | 1.762 | 5.266 | 1.40E−07 |
| 8 | rs1365032 | 75715655 | A | ADD | 1043 | 0.668 | −4.404 | 1.07E−05 |
| 9 | rs7029403 | 85897708 | A | ADD | 1043 | 0.6088 | −4.387 | 1.15E−05 |
| 8 | rs1365031 | 75718745 | A | ADD | 1043 | 0.6718 | −4.323 | 1.54E−05 |
| 20 | rs10460623 | 56638627 | A | ADD | 1042 | 1.614 | 4.294 | 1.76E−05 |
| 8 | rs2016354 | 75722054 | A | ADD | 1043 | 0.6747 | −4.283 | 1.84E−05 |

TABLE 1-continued

Table 1: Univariate GWAS association (0-60 gwas sign SNPs n = 16)

| CHR | SNP | BP | A1 | TEST | NMISS | OR | STAT | P |
|---|---|---|---|---|---|---|---|---|
| 3 | rs83615 | 172794423 | G | ADD | 1041 | 1.708 | 4.246 | 2.18E−05 |
| 13 | rs17087682 | 70395009 | C | ADD | 1026 | 0.5474 | −4.191 | 2.78E−05 |
| 4 | rs7670729 | 84465114 | A | ADD | 1043 | 0.6516 | −4.161 | 3.17E−05 |
| 2 | rs10197959 | 230078358 | A | ADD | 1042 | 1.471 | 4.126 | 3.69E−05 |
| 14 | rs7150586 | 68913992 | A | ADD | 1042 | 1.448 | 4.122 | 3.75E−05 |
| 1 | rs1050492 | 224887123 | A | ADD | 1038 | 0.6549 | −4.12 | 3.79E−05 |
| 14 | rs10138313 | 68952145 | G | ADD | 1043 | 0.6915 | −4.119 | 3.81E−05 |
| 12 | rs1861872 | 14074193 | G | ADD | 1042 | 0.5062 | −4.095 | 4.22E−05 |
| 21 | rs2838735 | 45159710 | G | ADD | 1042 | 0.6882 | −4.085 | 4.41E−05 |
| 5 | rs34566 | 106628114 | G | ADD | 1042 | 0.6933 | −4.08 | 4.51E−05 |
| 7 | rs17152065 | 127861094 | A | ADD | 1043 | 0.5974 | −4.073 | 4.65E−05 |
| 2 | rs4364055 | 52907433 | A | ADD | 1042 | 0.5997 | −4.07 | 4.71E−05 |
| 8 | rs1581542 | 69376583 | A | ADD | 1043 | 0.6884 | −4.056 | 5.00E−05 |

Example 2

TABLE 2

Univariate analysis chi square (0-60 top hits n = 74)

(a):

| CHR | SNP | BP | A1 | TEST | NMISS | OR | STAT | Pvalue |
|---|---|---|---|---|---|---|---|---|
| 5 | rs11167764 | 141459249 | A | ADD | 1043 | 0.6976 | −2.975 | 0.002933 |
| 13 | rs3764147 | 43355925 | G | ADD | 1043 | 1.277 | 2.449 | 0.01434 |
| 5 | rs6556412 | 158719963 | A | ADD | 1043 | 1.212 | 2.079 | 0.03763 |
| 15 | rs16950687 | 65251067 | G | ADD | 1043 | 1.229 | 2.063 | 0.03908 |

(b):

| SNP | Chromosome | P value | OR | Gene of Interest |
|---|---|---|---|---|
| rs11167764 | 5 | 0.003 | 0.7 | NDFIP1 |
| rs3764147 | 13 | 0.01 | 1.3 | C13orf31 |
| rs6556412 | 5 | 0.04 | 1.2 | IL12B |
| rs16950687 | 15 | 0.04 | 1.2 | SMAD3 |

Example 3

Combination of Genetic, Clinical and Immune Markers Predict Surgery

The inventors identified genetic and phenotypic associations with need for surgery and time to surgery within 5 years of diagnosis, and built a predictive model for need for surgery. The ability to identify patients with Crohn's disease (CD) who are at highest risk for rapid progression to surgery is invaluable in guiding initial therapeutic choices.

The need for surgery was defined as intestinal resection within 5 years of diagnosis. Genotyping was performed on 1103 subjects using Illumina-based Genome-wide technology. Univariate and multivariate analyses tested genetic associations with need for surgery. Time to surgery was analyzed using Cox-proportional hazard. All analyses were performed by testing known IBD susceptibility loci (n=74) and also by performing a GWA study. Clinical and serologic immune phenotypes as measured by antibody sum were included in the logistic regression analyses and used to build a predictive model of need for surgery.

The inventors found that surgery occurred within 5 years of diagnosis in 39% of total subjects. The median time to surgery was 6 months. In the univariate analyses, four known CD susceptibility loci (Table 2 herein) were associated with need for surgery within 5 years (p<0.05). The HLA region was the only known susceptibility loci associated with time to surgery (p=0.02). GWA revealed 16 putative loci associated with need for surgery and 51 with time to surgery at a level of nominal association at the genome-wide level (p<5×10$^{-5}$). GWA identified SNPs at chromosome (chr.) 4q31 and at chr. 7p21 (containing the glucocorticoid induced transcript 1 gene) showed the most significant association with need for surgery within 5 years (Odds ratio [OR]=1.8; p=1.4×10$^{-7}$) and time to surgery (Hazard Ratio [HR]=1.7; p=1.0×10$^{-7}$), respectively. Two loci: rs6556412 (IL-12B, chr. 5q33) (OR=0.74; p<0.001) and the chr. 4q31 region (OR=1.51; p=0.003) remained independently associated with surgery in the logistic regression analyses. Small bowel location (OR=3.2; p<0.0001), age at diagnosis (OR=2.88; p<0.0001) and antibody sum (OR=1.64; p<0.0001) were also associated with need for surgery. A predictive model for surgery incorporating all 5 variables had an area under the curve of 0.770. Thus, the inventors found IL12B is associated with need for surgery in CD. The identification of genetic, clinical and immune risk factors that can predict need for surgery can help clinicians and patients choose appropriate treatments based on an individual's risk of early surgery.

Example 4

The ability to identify patients with Crohn's disease (CD) at highest risk of surgery would be invaluable in guiding therapy. Genome-wide association (GWA) studies have identified multiple IBD loci with unknown phenotypic consequences. Methods: Surgery was defined as intestinal resection within 5 years of diagnosis. Genotyping was performed on 1115 subjects using Illumina-based Genome-wide technology. Univariate and multivariate analyses tested genetic associations with need for surgery. Time to surgery was analyzed using Cox-proportional hazard. Analyses were performed by testing known CD loci (n=71) and by performing a GWA study. Clinical and serologic variables were included to build predictive models for surgery. Results: Surgery occurred within 5 years in 21% of subjects at a median time of 12 months. Four susceptibility loci were associated with surgery (IL12B, C13orf31, 21q21, IBD5). GWA identified novel putative loci associated with surgery, 7q21 (CACNA2D1) and 16q23 (ZNRF1, LDHD). The most predictive model for surgery which included clinical, serologic and genetic factors had an AUC of 0.78. Forty percent of patients in the highest risk group progressed to surgery within 60 months in the best predictive model. Conclusion: Progression to surgery is faster in CD patients with both genetic and clinical risk factors. IL12B is independently associated with need and time to surgery in CD patients.

Example 5

Patient Population

A total of 1115 well characterized CD patients from both the Adult and Pediatric IBD Centers at CSMC, The Western Regional Research Alliance for Pediatric IBD and Wisconsin were included in this study. Surgery was defined as intestinal resection only for penetrating or stricturing CD. Perianal surgery and stricturoplasty were excluded. This study was approved by the IRB at all participating sites.

Example 6

Phenotyping

All data was collected by chart review and stored in a secured database. For the purpose of this study, phenotype was defined as all variables that were not genetic.
Clinical Phenotype:
These included demographic and clinical variables: age, gender, disease duration, age at diagnosis, date of diagnosis, disease location, type of disease complication (stricturing and/or internal penetrating disease), date of disease complication, type of CD surgery, time from diagnosis to CD surgery or time from diagnosis to last follow up in those patients who have not required surgery.
Immune Phenotype:
Serum was collected on all patients and analyzed at CSMC. Serum immune responses: anti-*Saccharomyces Cereviciae* antibodies (ASCA IgG and IgA), perinuclear antinuclear cytoplasmic antibody (pANCA), anti-flagellin (anti-CBir1), anti-outer membrane porin C (anti-OmpC) and anti-Pseudomonas fluorescens-associated sequence 12 (anti-12) were analyzed blinded to therapeutic responsiveness by ELISA as previously described (5, 25). Antibody sum score was calculated for each patient based on how many positive antibodies an individual patient had. Scores range from 0 to 5 ((ASCA IgA and IgG, anti-CBir1, anti-OMPc and anti-12), and for the purpose of analysis scores were then grouped into a score of 0 or 1, 2 or 3, and 4 or 5 positive. ANCA was analyzed separately given that ANCA has been shown to be negatively associated with CD resective surgery (26)

Example 7

Genotype

Genotyping was performed at the Medical Genetics Institute at CSMC using the Illumina Human610 platform (n=887) and Children's Hospital of Philadelphia (CHOP) using the Illumina Human550 platform (n=228) (27). Genotyping for the 3 common CD associated NOD2 SNPs (SNPs 8, 12 and 13) was performed using TaqMan MGB platform (28). For the purpose of quality control, SNPs with a minor allele frequency (MAF)<0.05, genotype failure rate>0.10, HWE p-value<$10^{-5}$ and missing rate of >0.1 were excluded from the analysis. Following quality control, 486,926 SNPs were available in all data sets for analysis. Principal components (PC) analysis (using EIGENSTRAT) was conducted to examine population stratification (29). As the inventors examined the first 10 PCs with the default options provided by EIGENSTRAT, we observed that 66 patients were identified as outliers and the direction of the first 2 PCs shown in multidimensional scatter plot were separate. Thus, the inventors excluded the 66 patients identified as outliers, and corrected for population stratification by adding the first 2 PCs as covariates in the model of association analysis.

Example 8

Statistical Analysis

A. Need for Surgery within 60 Months
Genome-Wide Association Studies
The inventors' primary outcome was resective surgery within 60 months. In order to identify genetic factors that influence the need for surgery, they performed genome-wide single SNP association. For each SNP, an additive model was assumed. With a logistic regression model having 2 PCs and a SNP, PLINK was used to evaluate the association between the need for surgery and each single SNP. Genomic inflation factor $\lambda$ of 1.00422 reveals no significant population stratification. The SNPs with a p-value<$10^{-5}$ from the GWAS were considered as significant for this outcome and carried forward to additional analyses. For the 71 CD susceptibility loci (referred below as "top hits" that were reported in the latest published CD meta-analysis, the SNPs that had a p-value<0.05 in the analyses above were considered "significant" for association with need for surgery (20). NOD2, (SNP 8, 12 and 13) because of multiple disease predisposition alleles and prior literature, was tested separately using the chi-square test. Odds Ratio (OR) and 95% Confidence intervals (95% CI) were calculated by comparing the odds of surgery in the patients with a specific genotype versus those without the genotype.
Predictive Models of Need for Surgery
Models to predict need for surgery were built using multiple logistic regression, combining the following variables: A: Genetics; Top Hits p<0.05, Genome-wide SNPs p<$10^{-5}$, and NOD2 status (any NOD2 SNP with a p≤0.05 was considered positive), B: Serologies; Antibody Sum Score 0, 1 or 2, 3 or 4, 5, and ANCA status (positive or negative) C: Clinical: age at diagnosis (<16 vs.>16 yrs), disease duration, gender, small bowel location. Using these variables, 5 model strategies were constructed:
I. Genetics only (excluding NOD 2 status)
II. Clinical variables only
III. Clinical+Serology
IV. Genetics+Clinical
V. Genetics (including NOD2 status)+Clinical+Serology The final predictive model of the need for surgery for each strategic model was determined by using stepwise model selection method. The area under the Receiver Operating Characteristic curve (AUC) was used as a measure of the predictive performance of the final model. The likelihood based pseudo-R squared from the logistic regression model was used to measure the strength of association as well as the proportion of variance of the outcome accounted by the model's independent variables (30). The data analyses were generated using SAS/STAT software, Version 9.2 of the SAS System for Windows.

B. Time to Surgery
Survival Genome-Wide Association Analysis:

In order to determine influential genetic factors to time to surgery, survival genome-wide single SNP association was performed by assuming an additive genetic model for each SNP. The survival GWAS employed Cox regression modeling, utilizing 2PCs and SNPs as independent variables, and was performed by R package 'survival' (31). The SNPs with a p-value<$10^{-5}$ from the GWAS were considered as "significant" for this outcome and carried forward for additional analyses. All hazard rations (HR) were expressed as a point estimate with 95% confidence interval. For the known 71 CD 'SNPs', association with time to surgery was considered significant if the p-value was ≤0.05. The AUCs for each of the models were compared to determine if there was statistical evidence of differing utilities between the models (32).

Predictive Models of Time to Surgery

Predictive models of time to surgery were built from the 5 strategic models described above. Patients who had surgery at diagnosis or within 3 months of diagnosis were excluded from this particular analysis. The final predictive model of time to surgery for each strategic model was determined by stepwise model selection method. In order to identify if disease progression is important for stratifying patients into more effective treatment paradigms, the patients were divided into 3 subgroups based on 25% and 75% quartiles of the risk score, which is the sum of variables in the final predictive model. Survival curves for each subgroup were plotted by Kaplan-Meier estimator of survival probability and were tested by the log-rank test to test whether the survival curves were significantly different among subgroups of patients.

Example 9

Patient Demographics

Table 3 illustrates the key demographic data for all patients. The mean age at diagnosis for this cohort was 15 years of age and more than 50% of the patients were diagnosed at 16 years of age or younger. Approximately 75% of patients had small bowel involvement and just over 50% had complicated disease behaviors as of last follow up or at time of surgery. Four hundred and forty-four of the 1115 (40%) had undergone resective surgery in our cohort with a median (range) time to surgery of 45.5 (0-516.8) months. A total of 219 or 21% of patients underwent surgery between diagnosis and 60 months of follow up with a median (range) of 12 (0-60) months. NOD2 'positivity' (carrier for at least 1 of the 3 common CD associated NOD2 risk alleles) was found in 33% of CD patients consistent with previously published data (13-18). ANCA status was negative in 79% of patients, and Antibody Sum groups 0, 1, 2, 3 and 4, 5 were observed in 48%, 36% and 16%, respectively

TABLE 3

Patient Demographics

| Clinical Variable | |
|---|---|
| Total Cohort N | 1115 |
| Gender: Males N (%) | 597 (53) |
| Median disease duration at last follow up (months [range]) | 38.1 [0-541.7] |
| Median age at diagnosis (years [range]) | 15 [1-77] |
| Diagnosis ≤16 years of age N (%) | 632 (57) |
| Small bowel involvement N (%) | 843 (76) |
| Stricturing and/or Internal Penetrating disease N (%) | 454 (51) |
| Antibody Sum groups N (%) | |
| 0, 1 | 535 (48%) |
| 2, 3 | 402 (36%) |
| 4, 5 | 178 (16%) |
| NOD2 positive N (%) | 321 (33%) |

Example 10

Need for Respective Surgery within 60 Months

Single SNP Genome Wide Associations

From the targeted analysis of the 71 known CD susceptibility loci, 6 were found to be associated (p≤0.05) with need for surgery (Table 4). Table 5 lists the results of the single SNP associations (with a p value<$5\times10^{-5}$ identified in the genome-wide approach. The association with the need for surgery at the IL12B locus is observed in both the known susceptibility loci and genome-wide analyses, and remains significant when corrected for multiple tests in the known susceptibility loci ($p_c$=0.001). No association was seen between any of the NOD2 SNPs and need for surgery.

TABLE 4

Known CD susceptibility loci: SNPs associated with need for surgery (P < 0.05)

| SNP | Loci | Risk Allele* | Positional Candidate Gene (s) of Interest | OR | 95% CI | P value |
|---|---|---|---|---|---|---|
| rs6556412 (SEQ. ID. NO.: 1) | 5q33 | A | IL12B | 1.6 | 1.3-2.0 | 1.478 × $10^{-5}$ |
| rs3936503 | 10p11 | G | CREM | 0.7 | 0.6-0.9 | 0.0066 |
| rs359457 | 5q35 | A | CPEB4 | 0.8 | 0.6-1.0 | 0.0155 |
| rs3764147 | 13q14 | G | C13orf31 | 1.3 | 1.0-1.6 | 0.0219 |
| rs1736148 | 21q21 | G | — | 1.3 | 1.0-1.6 | 0.0357 |
| rs4788084 | 16p11 | G | IL27, SH2B1, EIF3C, LAT, CD19 | 0.8 | 0.6-1.0 | 0.0366 |

— No gene of interest identified
*Risk allele as defined as risk for CD

TABLE 5

Genome-wide analysis:: SNPs associated with need for surgery (p < 5.0 × 10⁻⁵)

| SNP | Loci | Risk Allele | Positional candidate Gene(s) of Interest | OR | 95% CI | P value |
|---|---|---|---|---|---|---|
| rs11978472 | 7q21 | A | CACNA2D1 | 0.6 | 0.4-0.7 | $8.418 \times 10^{-7}$ |
| rs2253755 | 10q26 | A | PLEKHA1, HTRA1, ARMS2 | 0.5 | 0.4-0.7 | $7.13 \times 10^{-6}$ |
| rs11863071 | 16q24 | G | — | 1.8 | 1.4-2.3 | $8.713 \times 10^{-6}$ |
| rs6556412 | 5q33 | A | IL12B * | 1.6 | 1.3-2.0 | $1.478 \times 10^{-5}$ |
| rs12520590 | 5q33 | C | GALNT1, SAP30L | 1.7 | 1.3-2.1 | $1.724 \times 10^{-5}$ |
| rs13403289 | 2q31 | A | ZNF385B, SESTD1 | 0.6 | 0.4-0.8 | $1.924 \times 10^{-5}$ |
| rs2226674 | 21q21 | G | — | 0.6 | 0.4-0.7 | $2.208 \times 10^{-5}$ |
| rs11235508 | 11q13 | G | CLPB, PDE2A | 1.9 | 1.4-2.6 | $2.518 \times 10^{-5}$ |
| rs11647106 | 16q24 | G | — | 1.8 | 1.3-2.3 | $2.769 \times 10^{-5}$ |
| rs2295655 | 14q32 | A | miRNA ** | 1.6 | 1.3-2.0 | $4.016 \times 10^{-5}$ |
| rs4709724 | 6q26 | G | QK1 | 0.6 | 0.5-0.8 | $4.086 \times 10^{-5}$ |
| rs10955078 | 8q22 | G | SDC2, PGCP | 1.6 | 1.3-2.0 | $4.217 \times 10^{-5}$ |
| rs1528934 | 7q21 | A | ZNF804B | 1.6 | 1.3-2.0 | $4.406 \times 10^{-5}$ |
| rs2765122 | 13q12 | G | MIPEP, PCOTH, SPATA13, C1QTNF9B | 0.5 | 0.4-0.7 | $4.8 \times 10^{-5}$ |
| rs550619 | 2p24 | G | APOB | 1.8 | 1.4-2.5 | $4.919 \times 10^{-5}$ |

* Known IBD susceptibility locus
** miRNA—micro-RNA cluster.

Predictive Models of Need for Surgery

Five different predictive models on the need for surgery were developed using logistic multiple regression. Model I (Genetics only but excluding NOD2) (Table 6) examined the significance of known CD susceptibility loci (p≤0.05) (table 2) together with the genome-wide identified loci (p<10⁻⁵) (Table 5). IL12B remained independently associated with need for surgery (p=0.0002).

Model II (clinical only) examined the associations of demographics and clinical variables together (age at diagnosis, gender and small bowel disease location) with need for surgery within 60 months of diagnosis. Older age at diagnosis (OR [95% CI]=1.9 [1.4-2.5] p=7.83e-05) and small bowel disease (OR [95% CI]=4.4 [2.6-7.4] p=2.6e-08) were associated with need for surgery. In MODEL III (clinical+serologies); older age at diagnosis (OR [95% CI]=1.8 [1.3-2.5] p=0.0002), small bowel disease (OR [95% CI]=3.5 [2.0-5.9] p=5.41e-06) were associated with need for surgery. Low antibody sum score of 0, 1 was protective against surgery (OR [95% CI]=0.6 [0.4-0.8] p=0.001). In Model IV (genetics+clinical), all loci from Model 1, with the exception of the 16p11, (IL27) locus, remained significantly associated with need for surgery as was age at diagnosis and small bowel disease location, with odds ratios similar to those seen in models I and II. Table 7 illustrates the logistic regression for Model V (Genetics+NOD2 status+clinical+serologies). NOD2 status was not associated with need for surgery. Low antibody sum was protective against surgery. IL12B remained a significant predictor of surgery throughout all models. Table 8 compares the AUC and pseudo R² for the 5 predictive models. The inventors did also look at the AUC and pseudo R² for a model that included disease complication (internal penetrating and or stricturing disease behavior) as part of the clinical variables in addition to genetics and serologies. As expected, given the known association between disease complication and surgery, the AUC (95% CI) was the highest for this additional model at 0.83 (0.81-0.86) and pseudo R² of 0.23.

They then compared the AUCs for each of the models to see if there was statistical evidence of differing utilities between the models: Model 1 (genetics only) vs. Model 2 (clinical only); p=0.03, Model 1 (genetics only) vs. Model 4 (genetics+clinical); p=0.04, Model 2 vs. 4; p=1.5×10⁻⁵ and Model 3 (clinical+serologies) vs. 4; p=0.002. In contrast, there was no difference between Models 1 or 2 vs. 3 or between Models 4 and 5 (genetics+NOD2+clinical+serologies). This suggests that a model that includes both genetics and clinical is more predictive than genetics alone or clinical alone Serologies or NOD2 status did not add significantly to the prediction of the model.

TABLE 6

Model I: Genetics Only Logistic Regression

| SNP | Top Hit SNP (TH) or GWAS SNP (GW) | Gene of Interest | OR | 95% CI | P value |
|---|---|---|---|---|---|
| rs6556412 (SEQ. ID. NO.: 1) | TH | IL12B | 1.5 | 1.2-1.9 | 0.0002 |
| rs359457 | TH | CPEB4 | 0.7 | 0.6-0.9 | 0.004 |
| rs11978472 | GW | CACNA2D1 | 0.5 | 0.4-0.7 | $1.1135 \times 10^{-6}$ |
| rs3936503 | TH | CREM | 0.7 | 0.6-0.9 | 0.0144 |
| rs2253755 | GW | PLEKHA1 | 0.5 | 0.4-0.7 | $5.711 \times 10^{-5}$ |
| rs3764147 | TH | C13orf31 | 1.3 | 1.0-1.6 | 0.0402 |

TABLE 6-continued

Model I: Genetics Only Logistic Regression

| SNP | Top Hit SNP (TH) or GWAS SNP (GW) | Gene of Interest | OR | 95% CI | P value |
|---|---|---|---|---|---|
| rs4788084 | TH | IL27 | 0.8 | 0.6-1.0 | 0.0577 |
| rs11863071 | GW | — | 1.8 | 1.4-2.3 | $3.7863 \times 10^{-5}$ |

— No gene of interest identified

TABLE 7

Model V (genetics + NOD2 status + clinical + serologies) Logistic Regression

| Independent Variable | OR | 95% CI | P value |
|---|---|---|---|
| Genetics* | | | |
| SNP (gene of interest) | | | |
| rs6556412 (IL12B) | 1.6 | 1.2-2.0 | 0.0007 |
| rs359457 (CPEB4) | 0.6 | 0.5-0.9 | 0.0016 |
| rs11978472 (CACNA2D1) | 0.6 | 0.4-0.7 | $1.3364 \times 10^{-5}$ |
| rs3936503 (CREM) | 0.7 | 0.5-0.9 | 0.0205 |
| rs2253755 (PLEKHA1) | 0.5 | 0.3-0.6 | $1.6205 \times 10^{-6}$ |
| rs11863071 (16q24) | 1.6 | 1.2-2.2 | 0.0025 |
| rs1736148 (21q21) | 1.4 | 1.1-1.9 | 0.0072 |
| Clinical | | | |
| Age at diagnosis | 2.1 | 1.4-3.1 | $5.5603 \times 10^{-5}$ |
| Small bowel disease | 3.3 | 1.8-6.0 | $7.9579 \times 10^{-5}$ |
| Serology | | | |
| AB sum 0, 1 | 0.5 | 0.4-0.8 | 0.0019 |

*See Table 4 for Top Hits vs. GWAS origin of SNP

TABLE 8

AUC and pseudo $R^2$ for the 5 models

| Logistic Regression Model | AUC | 95% CI | Pseudo $R^2$ |
|---|---|---|---|
| I. Known CD susceptibility loci and genome-wide identified loci | 0.71 | 0.67-0.75 | 0.0963 |
| II. Clinical only: SB, gender, Age at Diagnosis, | 0.66 | 0.62-0.69 | 0.0586 |
| III. Clinical + Serologies | 0.69 | 0.65-0.72 | 0.0721 |
| IV. Genetics + Clinical | 0.76 | 0.73-0.80 | 0.1465 |
| V. Genetics + NOD2 status + Clinical + Serologies | 0.78 | 0.74-0.81 | 0.1610 |

Example 11

Time to Respective Surgery

Single SNP Genome Wide Associations

The total number of patients included in the time to surgery analyses was 983 after principal component analysis and after exclusion of patients who underwent surgery at or within 3 months of diagnosis. The known CD susceptibility loci and novel SNPs from the genome-wide analyses associated with time to surgery are shown in Tables 9 and 10.

TABLE 9

Known CD susceptibility loci: SNPs associated with time to surgery (P < 0.05)

| SNP | Loci | Risk Allele | Gene (s) of interest | Hazard Ratio | 95% CI | P value |
|---|---|---|---|---|---|---|
| rs6556412 | 5q33 | A | IL12B | 1.5 | 1.2-1.9 | 0.0006 |
| rs12521868 | 5q31 | A | SLC22A4, SLC22A5, IRF1, IL3 | 1.3 | 1.0-1.6 | 0.0442 |
| rs1736148 | 21q21 | G | — | 1.3 | 1.0-1.6 | 0.0495 |
| rs3764147 | 13q14 | G | C13orf31 | 1.3 | 1.0-1.6 | 0.0503 |

TABLE 10

Genome-wide analysis: SNPs associated with time to surgery (p < $5.0 \times 10^{-5}$)

| SNP | Loci | Risk Allele | Gene (s) of Interest | Hazard Ratio | 95% CI | P value |
|---|---|---|---|---|---|---|
| rs7195303 | 16q23 | G | ZNRF1, LDHD, ZFP1, BCAR1, CTRB1/2 | 2.1 | 1.5-2.8 | $9.06 \times 10^{-6}$ |
| rs471073 | 15q25 | A | AKAP13, KLHL25, MIR1276 | 1.8 | 1.4-2.3 | $1.6973 \times 10^{-5}$ |
| rs9346964 | 6q26 | A | QK1 | 1.7 | 1.3-2.1 | $1.8184 \times 10^{-5}$ |
| rs6469010 | 8q23 | G | ZFPM2 | 1.8 | 1.4-2.4 | $1.9105 \times 10^{-5}$ |
| rs4901140 | 14q21 | G | C14orf25, TTC6 | 1.7 | 1.4-2.3 | $1.9378 \times 10^{-5}$ |
| rs11583755 | 1p36 | A | THAP3, TAS1R1, PLEKHG5 | 0.6 | 0.4-0.7 | $2.2889 \times 10^{-5}$ |
| rs11235508 | 11q13 | G | CLPB, PDE2A | 1.9 | 1.4-2.5 | $2.5083 \times 10^{-5}$ |
| rs1998828 | 13q21 | A | — | 1.6 | 1.3-2.0 | $2.7091 \times 10^{-5}$ |
| rs2894207 | 6p21 | G | HLA** | 1.6 | 1.3-2.1 | $2.8892 \times 10^{-5}$ |
| rs9548517 | 13q13 | A | FREM2, STOML3 | 1.8 | 1.4-2.4 | $3.0068 \times 10^{-5}$ |
| rs2765122 | 13q12 | G | PCOTH, SPATA13, C1QTNF9B, MIPEP | 0.5 | 0.3-0.7 | $3.8064 \times 10^{-5}$ |
| rs13403289 | 2q31 | A | ZNF385A, SESTD1 | 0.6 | 0.5-0.8 | $4.0984 \times 10^{-5}$ |
| rs12531232 | 7q21 | A | ZNF804B | 1.6 | 1.3-2.0 | $4.3313 \times 10^{-5}$ |
| rs823559 | 12q23 | A | SLC5A8, ANO4 | 2.0 | 1.4-2.8 | $4.8477 \times 10^{-5}$ |
| rs6957717 | 7 | A | SKAP2, C7orf71 | 0.6 | 0.4-0.7 | $4.9161 \times 10^{-5}$ |

**Known CD susceptibility locus

Predictive Models of Need for Surgery

Figure 1B:
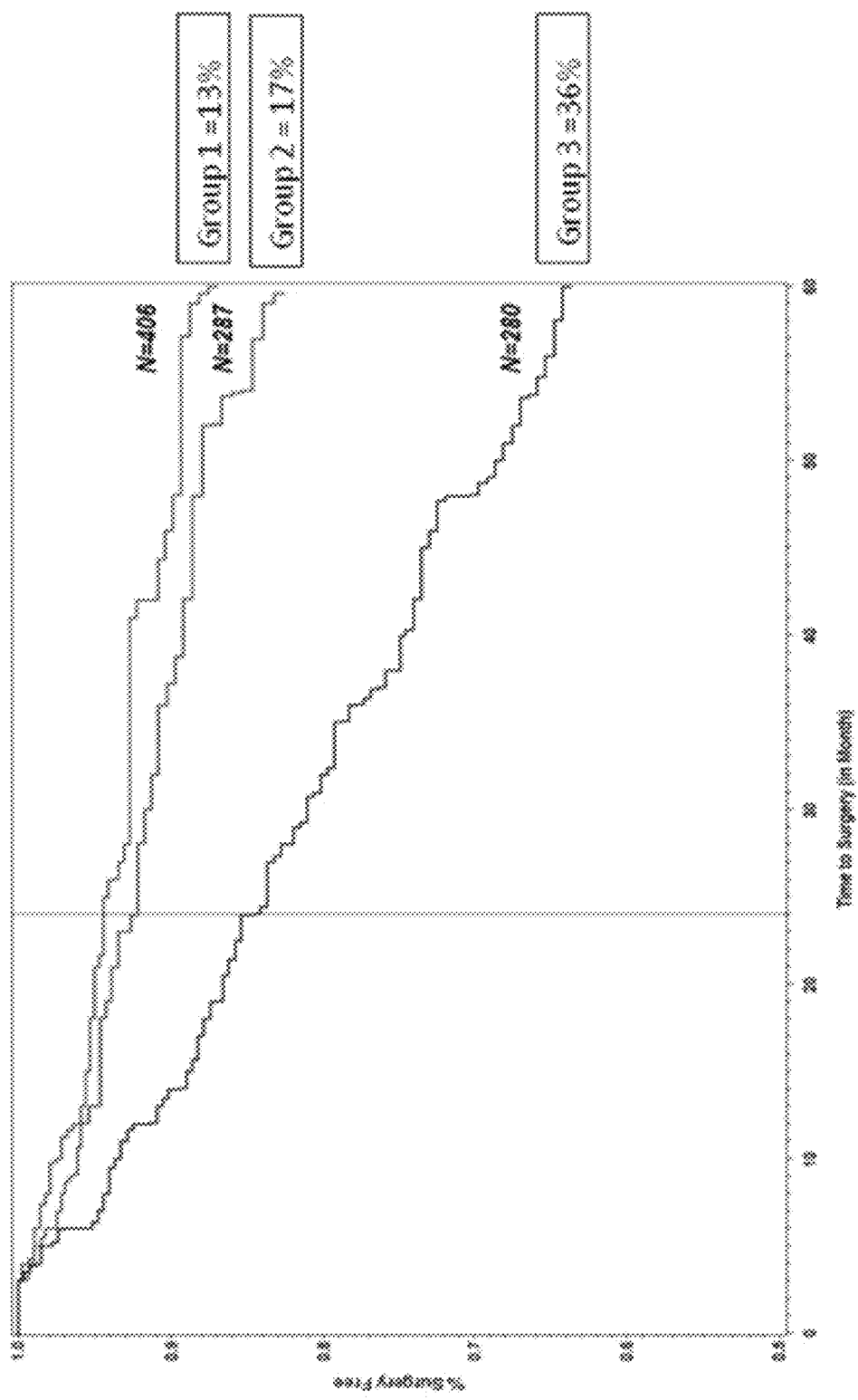
FIG. 1B illustrates, in accordance with an embodiment of the invention, survival curves for the three strata for model IV (clinical+genetics).
Figure 1C:
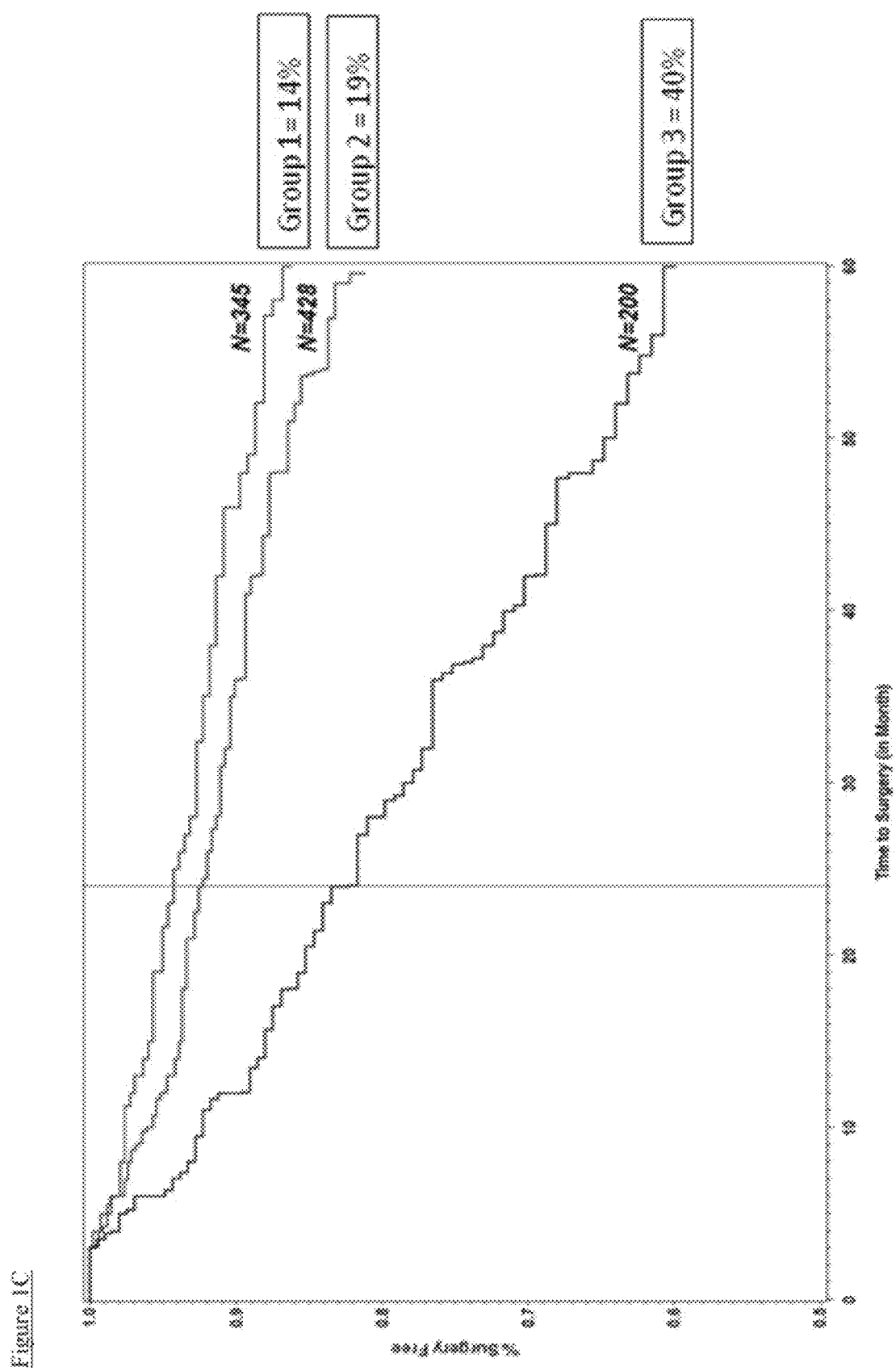
FIG. 1C illustrates, in accordance with an embodiment of the invention, survival curves for the three strata for model V (genetics+NOD2+clinical+serologies).

Predictive models of time to surgery were developed using the same 5 model strategies outlined earlier for predicting the need for surgery. The goal of these analyses were to first determine using Cox Hazard Regression modeling the variables that were independently associated with progression to surgery and then to use log rank testing to compare the survival curves for different risk strata within each model in order to determine which patients progressed to surgery faster. The 3 risk strata were derived based on the sum of the variables in the final predictive models: strata 1=≤the 25% quartile of the sum of variables, strata 2=between 25% and 75% quartiles of the sum of variables and strata 3=≥75% quartile of the sum of variables. Each clinical and serology variable gets a score of 1 or 0 and an additive genetic model was adopted. Table 9 shows the hazard ratios for the genetics only model (Model I) and FIG. 1A illustrates the survival curves for the 3 risk strata in this model. The proportion of patients in the lowest strata score that progressed to surgery within 60 months was significantly less (15%) than the medium (22%) and highest strata (36%) (log rank test: $p=1.6\times10^{-10}$). As compared to the predictors of need for surgery for model II (clinical only), only small bowel predicted time to surgery (HR [95% CI] 3.3 [1.9-5.6] $p=1.28\times10^{-5}$) and age at diagnosis did not. For model IV (genetics+clinical) all 4 SNPs from the genetics only model along with small bowel disease location and age at diagnosis were associated with time to surgery (HR [95% CI]=1.5 [1.1-2.0] p=0.02 and 3.2 [1.9-5.4], $p=2.22\times10^5$, respectively). Table 10 shows the hazard ratios for model V (genetics+NOD2+clinical+serologies). Antibody sum score 2, 3, NOD2, 3 other loci (including IL12B) in addition to small bowel disease location and age at diagnosis were all associated with time to surgery. FIGS. 1B and 1C illustrate the survival curves for the 3 strata for model IV (clinical+genetics) and model V (genetics+NOD2+clinical+serologies). In all 3 models, patients in the highest risk group progressed to surgery faster (p<0.0001). For all 3 models depicted in figure form, there is a greater than 20% difference in frequency of progression to surgery between the lowest risk and highest risk strata.

TABLE 11

Model I: Genetics only; Cox proportional Regression

| SNP | Top Hit SNP (TH) or GWAS SNP (GW) | Gene (s) of Interest | HR | 95% CI | P value |
|---|---|---|---|---|---|
| rs6556412 | TH | IL12B | 1.5 | 1.0-1.6 | 0.0006 |
| rs12521868 | TH | IBD5 SLC22A4, SLC22A5 | 1.3 | 1.2-1.9 | 0.0318 |
| rs7195303 | GW | ZNRF1, LDHD | 2.1 | 1.5-2.9 | $10\times10^{-5}$ |
| rs1736148 | TH | 21q21 | 1.3 | 1.0-1.6 | 0.0310 |

TABLE 12

Model V: Genetics + NOD2 + clinical + serologies; Cox proportional regression

| Independent Variable | HR | 95% CI | P value |
|---|---|---|---|
| Genetics SNP and gene of interest | | | |
| rs6556412 (IL12B) | 1.5 | 1.2-2.9 | 0.0006 |
| rs7195303 (ZNRF1, LDHD) | 2.2 | 1.5-3.1 | $3.0456\times10^{-5}$ |

TABLE 12-continued

Model V: Genetics + NOD2 + clinical + serologies; Cox proportional regression

| Independent Variable | HR | 95% CI | P value |
|---|---|---|---|
| rs1736148 (21q21) | 1.4 | 1.1-1.8 | 0.0042 |
| NOD2 positive | 1.5 | 1.1-2.2 | 0.0150 |
| Clinical | | | |
| Age at Diagnosis | 1.5 | 1.1-2.2 | 0.0135 |
| Small bowel location | 2.4 | 1.4-4.3 | 0.0019 |
| Serologies | | | |
| AB Sum 2, 3 | 1.5 | 1.1-2.1 | 0.0226 |

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

1. Cosnes J, Cattan S, Blain A et al. *Long-term evolution of disease behavior of Crohn's disease*. Inflammatory Bowel Diseases 2002; 8:244-50.
2. Cosnes J, Nion-Larmurier I, Beaugerie L et al. Impact of the increasing use of immunosuppressants in Crohn's disease on the need for intestinal surgery. Gut 2005. 54:237-41.
3. Beaugerie L, Seksik P, Nion-Larmurier I et al. *Predictors of Crohn's disease*. Gastroenterology 2006; 130:650-6.
4. Dubinsky M C, Lin Y C, Dutridge D et al. Serum immune responses predict rapid disease progression among children with Crohn's disease: immune responses predict disease progression. Am J Gastroenterol 2006; 101:360-7.
5. Dubinsky M C, Kugathasan, Mei L et al. Increased immune eactivity predicts aggressive complicating Crohn's disease in children. Clin Gastro and Hep 2008: 6:1105-11.
6. Papp M, Altorjay I, Dotan N et al. New serological markers for inflammatory bowel disease are associated with earlier age at onset, complicated disease behavior, risk for surgery, and NOD2/CARD15 genotype in a Hungarian IBD cohort. Am J Gastroenterol 2008; 103: 665-681
7. Ferrante M, Henckaerts L, Joossens M et al. New serological markers in inflammatory bowel disease are associated with complicated disease behavior. Gut 2007; 56:1394-403
8. Sands B E, Arsenault J E, Rosen M J et al. *Risk of early surgery for Crohn's disease: implications for early treatment strategies*. Am J Gastroenterol 2003; 98:2712-8.
9. Amre D K, Lu S E, Costea F et al. Utility of serological markers in predicting the early occurrence of complications and surgery in pediatric Crohn's disease patients. Am J Gastroenterol 2006; 101:645-52.
10. Mow W S, Vasiliauskas E A, Lin Y C et al. Association of antibody responses to microbial antigens and complications of small bowel Crohn's disease. Gastroenterology 2004; 126:414-24.
11. Arnott I D, Landers C J, Nimmo E J et al. Sero-reactivity to microbial components in Crohn's disease is associated with disease severity and progression, but not NOD2/CARD15 genotype. Am J Gastroenterol 2004; 99:2376-84.
12. Siegel C A, Siegel L S, Hyams J S et al. A Real-Time tool to display the predicted disease course and treatment response for children with Crohn's disease. Inflammatory Bowel Diseases 2011:17; 30-8.
13. Lesage S, Zouali H, Cezard J P et al. CARD15/NOD2 mutational analysis and genotype-phenotype correlation in 612 patients with inflammatory bowel disease. Am J of Hum Genet. 2002; 70:845-857.

14. Abreu M T, Taylor K D, Lin Y C et al. Mutations in NOD2 are associated with fibrostenosing disease in patients with Crohn's disease. Gastroenterology. 2002; 123:679-688.
15. Kugathasan S, Maresso K, Collins N et al. L1007Fsinc variant of CARD15/NOD2 is strongly associated with early onset and fibrostenosing behavior in pediatric Crohn's disease. Clin Gastroenterol Hepatol 2004; 2:1003-9.
16. Russell R K, Drummond H E, Nimmo E E et al. *Genotype-phenotype analysis in childhood-onset Crohn's disease: NOD2/CARD15 variants consistently predict phenotypic characteristics of severe disease.* Inflammatory Bowel Diseases 2005; 11:955-64.
17. Alvarez-Lobos M, Arostegui J I, Sans M et al. *Crohn's disease patients carrying Nod2/CARD15 gene variants have an increased and early need for first surgery due to stricturing disease and higher rate of surgical recurrence.* Ann Surg 2005; 242:693-700
18. Seiderer J, Brand S, Herrmann K A et al. *Predictive value of the CARD15 variant 1007fs for the diagnosis of intestinal stenoses and the need for surgery in Crohn's disease in clinical practice: results of a prospective study.* Inflammatory bowel diseases 2006; 12:1114-21
19. Henckaerts L, Van Steen K, Verstreken I et al. *Genetic risk profiling and prediction of disease course in Crohn's disease patients.* Clin Gastro Hep 2009; 7:972-980.
20. Franke A, McGovern D P, Barrett J C et al. *Genome-wide meta-analysis increases to 71 the number of confirmed Crohn's disease susceptibility loci.* Nature Genetics 2010; 1118-25.
21. Barrett J C, Hansoul S, Nicolae D L et al. *Genome-wide association defines more than 30 distinct susceptibility loci for Crohn's disease.* Nature Genetics 2008; 40:955-62
22. McGovern D P, Jones M R, Taylor K D et al. *Fucosyltransferase 2 (FUT2) non-secretor status is associated with Crohn's disease.* Human Molecular Genetics 2010. 19:3468-76.
23. Schunkert H, König I R, Kathiresan S et al. *Large-scale association analysis identifies 13 new susceptibility loci for coronary artery disease.* Nature Genetics 2011; 43:333-8
24. Okser S, Lehtimäki T, Elo L L et al. *Genetic variants and their interactions in the prediction of increased preclinical carotid atherosclerosis: the cardiovascular risk in young Finns study.* PLoS Genetics 2010. 6, 2010. UI: 20941391
25. Targan S R, Landers C J, Yang H et al. Antibodies to CBir1 flagellin define a unique response that is associated independently with complicated Crohn's disease. Gastroenterology 2005; 128:2020-8.
26. Vasiliauskas E A, Kam L Y, Karp L C et al. Marker antibody expression stratifies Crohn's disease into immunologically homogeneous subgroups with distinct clinical characteristics. Gut 2000; 47:487-96.
27. Gunderson K L, Steemers F J, Lee G et al. A genome-wide scalable SNP genotyping assay using microarray technology. Nat Genet 2005; 37:549-54
28. Morin P A, Saiz R, Monjazeb A: High-throughput single nucleotide polymorphism genotyping by fluorescent 5' exonuclease assay. Biotechniques 1999; 27: 538-552.
29. Price A L, Patterson N J, Plenge R M et al. Principal components analysis corrects for stratification in genome-wide association studies. Nat Genet. 2006; 38:904-9.
30. Stokes M E, Davis C S, Koch, G G. Categorical data analysis using the SAS system. $2^{nd}$ edition. SAS press, 2000, Cary, N.C., USA
31. Terry Therneau and original Splus→R port by Thomas Lumley (2011). Survival analysis, including penalized likelihood. R package version 2.36-5. http://CRAN.R-project.org/package=survival
32. Robin X, Turck N, Hainard A et al. "pROC: an open-source package for R and S+ to analyze and compare ROC curves". BMC Bioinformatics, 7, 77. DOI10.1186/1471-2105-12-77.
33. McGovern D P, Rotter J I, Mei L et al. Genetic epistasis of IL23/IL17 pathway genes in Crohn's disease. Inflammatory Bowel Diseases 2009:15; 883-9
34. Wang K, Zhang H, Kugathasan S, Annese V et al. *Diverse genome-wide association studies associate the IL12/IL23 pathway with Crohn Disease.* Am J Hum Genet 2009. 84:399-405
35. Haritunians T, Taylor K D, Targan S R et al. Genetic predictors of medically refractory ulcerative colitis. Inflammatory Bowel Diseases 2010:16:1830-40.
36. Dixon, A. L, Liang L, Moffatt M F et al., A genome-wide association study of global gene expression. Nat. Genet 2007; 39:1202-1207
37 Carboni G L, Gao B, Nishizaki M et alCACNA2D2-mediated apoptosis in NSCLC cells is associated with alterations of the intracellular calcium signaling and disruption of mitochondria membrane integrity. *Oncogene.* 2003; 22:615-26.
38. Wandall H H, Hassan H, Mirgorodskaya E et al. Substrate specificities of three members of the human UDP-N-acetyl-alpha-D galatosamine polypeptide N acetylgalactosaminyltransferase family GalNAc-T1, -T2, and -T3. *J Biol Chem.* 1997; 272:23503-14.
39. Sagara M, Kawasaki Y, Iemura S I et al. Asef2 and Neurabin2 cooperatively regulate actin cytoskeletal organization and are involved in HGF-induced cell migration. Laboratory of Molecular and Genetic Information, Institute for Molecular and Cellular Biosciences, University of Tokyo, Tokyo, Japan.
40. Lee H, Kim Y, Choi Y et al. Syndecan-2 cytoplasmic domain regulates colon cancer cell migration via interaction with syntenin-1. *Biochem Biophys Res Commun.* 2011; 27; 409:148-53.

The invention claimed is:

1. A method, comprising:
   providing a sample from a human with Crohn's Disease;
   utilizing an allelic discrimination assay or an oligonucleotide hybridization assay to analyze the sample for an "A" allele at position 513 of SEQ ID NO: 1;
   detecting the "A" allele at position 513 of SEQ ID NO: 1 in the sample;
   determining a need for surgical intervention in the human having the "A" allele at position 513 of SEQ ID NO: 1 in the sample; and
   treating the human by performing on the human determined to need surgical intervention a surgical intervention comprising intestinal resection.

2. The method of claim 1, further comprising determining the presence of two or more factors selected from the group consisting of clinical factors, serologic factors, genetic risk factors and combinations thereof.

3. The method of claim 1, further comprising determining the presence of anti-ASCA, pANCA, anti-Cbirl, anti-OmpC and/or anti-12.

4. The method of claim 1, further comprising detecting an "A" allele at position 251 of SEQ ID NO: 7.

5. The method of claim 1, further comprising detecting the presence of the "A" allele at position 201 of SEQ ID NO: 2, the "G" allele at position 301 of SEQ ID NO: 3, the "G" allele at position 251 of SEQ ID NO: 4, the "G" allele at position 401 of SEQ ID NO: 5, the "A" allele at position 501 of SEQ ID NO: 6, the "A" allele at position 251 of SEQ ID NO: 7, and the "G" allele at position 2156 of SEQ ID NO: 8.

6. The method of claim 1, further comprising detecting the "A" allele at position 201 of SEQ ID NO: 2.

7. The method of claim 1, further comprising detecting the "G" allele at position 301 of SEQ ID NO: 3.

8. The method of claim 1, further comprising detecting the "G" allele at position 251 of SEQ ID NO: 4.

9. The method of claim 1, further comprising detecting the "G" allele at position 401 of SEQ ID NO: 5.

10. The method of claim 1, further comprising detecting the "A" allele at position 501 of SEQ ID NO: 6.

11. The method of claim 1, further comprising detecting the "G" allele at position 2156 of SEQ ID NO: 8.

12. A method, comprising:
utilizing an allelic discrimination assay or an oligonucleotide hybridization assay to detect in a sample from a human with Crohn's disease, an "A" allele at position 513 of SEQ ID NO: 1;
identifying one or more risk factors selected from the group consisting of a diagnosis of Crohn's disease in the small bowel location, age of diagnosis, and risk serological factors;
prognosticating Crohn's disease with requiring surgery for treatment in the human having the "A" allele at position 513 of SEQ ID NO: 1 and the identified one or more risk factors; and
treating the human by performing surgery on the human prognosed with Crohn's disease requiring surgery for treatment, wherein the surgery comprises intestinal resection.

13. The method of claim 12, further comprising detecting one or more alleles selected from the group consisting of the "A" allele at position 201 of SEQ ID NO: 2, the "G" allele at position 301 of SEQ ID NO: 3, the "G" allele at position 251 of SEQ ID NO: 4, the "G" allele at position 401 of SEQ ID NO: 5, the "A" allele at position 501 of SEQ ID NO: 6, the "A" allele at position 251 of SEQ ID NO: 7, and the "G" allele at position 2156 of SEQ ID NO: 8.

14. The method of claim 12, wherein the risk serological factors are selected from the group consisting of anti-ASCA, pANCA, anti-Cbirl, anti-OmpC and anti-12.

15. The method of claim 12, further comprising detecting the presence of the "A" allele at position 201 of SEQ ID NO: 2, the "G" allele at position 301 of SEQ ID NO: 3, the "G" allele at position 251 of SEQ ID NO: 4, the "G" allele at position 401 of SEQ ID NO: 5, the "A" allele at position 501 of SEQ ID NO: 6, the "A" allele at position 251 of SEQ ID NO: 7, and the "G" allele at position 2156 of SEQ ID NO: 8.

16. The method of claim 12, further comprising detecting the "A" allele at position 251 of SEQ ID NO: 7.

* * * * *